(12) United States Patent
Lane et al.

(10) Patent No.: US 11,246,482 B2
(45) Date of Patent: Feb. 15, 2022

(54) VISUAL ACUITY EXAMINATION

(71) Applicant: Welch Allyn, Inc., Skaneateles Falls, NY (US)

(72) Inventors: John A. Lane, Weedsport, NY (US); Ervin Goldfain, Syracuse, NY (US); Megan Schneider, Syracuse, NY (US); Yaolong Lou, Singapore (SG); David L. Kellner, Baldwinsville, NY (US); Mathias Mereles, Stanhope, NJ (US); Chris R. Roberts, Skaneateles, NY (US); Tyson B. Whitaker, Arden, NC (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 286 days.

(21) Appl. No.: 16/175,249

(22) Filed: Oct. 30, 2018

(65) Prior Publication Data

US 2019/0125183 A1    May 2, 2019

Related U.S. Application Data

(60) Provisional application No. 62/579,462, filed on Oct. 31, 2017.

(51) Int. Cl.
*A61B 3/14* (2006.01)
*A61B 3/032* (2006.01)
(Continued)

(52) U.S. Cl.
CPC .............. *A61B 3/103* (2013.01); *A61B 3/005* (2013.01); *A61B 3/0025* (2013.01); *A61B 3/032* (2013.01); *A61B 3/14* (2013.01); *G06T 3/40* (2013.01)

(58) Field of Classification Search
CPC ....... A61B 3/028; A61B 3/032; A61B 3/0025; A61B 3/0033; A61B 3/0058;
(Continued)

(56) References Cited

U.S. PATENT DOCUMENTS

| 4,105,302 A | 8/1978 | Tate, Jr. |
| 5,596,379 A | 1/1997 | Kawesch |

(Continued)

FOREIGN PATENT DOCUMENTS

| JP | H09271461 A | 10/1997 |
| JP | 2000107127 A | 4/2000 |

(Continued)

OTHER PUBLICATIONS

The PCT Search Report and Written Opinion dated Feb. 25, 2019 for PCT Application No. PCT/US2018/058219, 10 pages.
(Continued)

*Primary Examiner* — Brandi N Thomas
(74) *Attorney, Agent, or Firm* — Lee & Hayes, P.C.

(57) ABSTRACT

A vision screening apparatus conducts a photorefraction ocular screening test to generate refractive error data. Based on the refractive error data, a Snellen equivalent is determined. An evaluated person distance from the vision screening apparatus is also determined and used to generate an adjusted optotype size. The vision screening apparatus displays the optotype, adjusted for the Snellen equivalent and the evaluated person distance.

15 Claims, 15 Drawing Sheets

(51) Int. Cl.
*A61B 3/103* (2006.01)
*A61B 3/00* (2006.01)
*G06T 3/40* (2006.01)

(58) Field of Classification Search
CPC ......... A61B 3/0325; A61B 3/036; A61B 3/06; A61B 3/103; A61B 3/113; A61B 3/18; A61B 5/117; A61F 2/16; A61F 9/00
See application file for complete search history.

(56) References Cited

U.S. PATENT DOCUMENTS

| | | | |
|---|---|---|---|
| 5,709,218 A | | 1/1998 | Holladay et al. |
| 5,914,772 A | * | 6/1999 | Dyer ................ A61B 3/028 351/222 |
| 9,173,565 B2 | | 11/2015 | Foster |
| 2012/0327369 A1 | | 12/2012 | Hytowitz |
| 2016/0120402 A1 | * | 5/2016 | Limon ................ A61B 3/0025 351/241 |
| 2017/0079523 A1 | | 3/2017 | Limon |
| 2017/0135571 A1 | | 5/2017 | Schubart et al. |

FOREIGN PATENT DOCUMENTS

| | | |
|---|---|---|
| JP | 2002209852 A | 7/2002 |
| JP | 2009005903 A | 1/2009 |
| JP | 2017143992 A | 8/2017 |
| WO | WO2010/117386 | 10/2010 |
| WO | WO2014195951 A1 | 12/2014 |
| WO | WO2016207684 A1 | 12/2016 |
| WO | WO2016132804 A1 | 10/2017 |

OTHER PUBLICATIONS

Japanese Office Action dated May 11, 2021 for Japanese Patent Application No. 2020-524131, a foreign counterpart to U.S. Appl. No. 16/175,249, 3 pages.
The Extended European Search Report dated Jun. 21, 2021 for European Patent Applicatin No. 18874081.5, 9 pages.
Meister, et al, "Introduction to Ophthalmic Optics", retrieved from <<http://64.50.176.246/files/introduction_to_ophthalmic_optics.pdf>>, Jun. 3, 2010, pp. 35-37, 44-45.

* cited by examiner

VISUAL ACUITY EXAMINATION

CROSS-REFERENCE TO RELATED APPLICATIONS

The present application is a nonprovisional application of U.S. Provisional Application No. 62/579,462, filed Oct. 31, 2017, the entire disclosure of which is incorporated herein by reference.

FIELD OF THE INVENTION

The present application relates to systems and methods for vision testing, and more particularly, to systems and methods for determining visual acuity.

SUMMARY

Visual acuity is a person's ability to identify characters at a particular distance. "Normal" visual acuity is generally regarded as being 20/20 vision. One example test for determining visual acuity involves an evaluated person reading characters on a Snellen chart. Typically, the evaluated person is positioned at a fixed distance from the Snellen chart, such as 10 feet away or 20 feet away. Each successive line has characters smaller than the characters in the line above. Visual acuity is then determined based on which line of characters the person can read. Example systems of the present disclosure include a vision screening apparatus configured to perform photorefraction ocular screening and display modified optotypes for visual acuity testing. In typical operation, results from photorefraction ocular screening are used to determine a Snellen equivalent. In some examples, the evaluated person's demographic information, pupil dynamics, and/or other information may also be used to determine such a Snellen equivalent. Based on an evaluated person's distance from the apparatus, an adjusted optotype may be displayed for a visual acuity test.

For instance, it is understood that most subjects fail visual acuity examinations because they have blurry vision for optical reasons, and that only a small percentage of subjects fail visual acuity examinations with relatively good eye optics (and, perhaps, a neurological issue). Accordingly, predicting an appropriate visual acuity for a given refractive error, and then having the subject read/identify optotypes according to the predicted visual acuity may confirm the acuity prediction and may also identify the minority of evaluated persons having neurological issues or other issues causing them to fail the visual acuity examination. Also, as will be described below, in examples in which the evaluated person's refractive error is below or above corresponding thresholds, the evaluated person may simply be referred to an eye care specialist without proceeding with the visual acuity examination.

Additionally, in some situations it may be necessary to perform critical line visual acuity screening examinations for occupational or worst-case testing (e.g., a vision test associated with obtaining a driver's license, etc.). In such example situations, the systems, devices, and/or methods described herein may be configured for administering such critical line visual acuity screening (e.g., pass/fail) examinations.

In one aspect, an example visual screening apparatus includes a processing unit and memory. The memory stores instructions that, when executed by the processing unit, cause the visual screening apparatus to: determine a Snellen equivalent based on an evaluation of a refractive error result; determine an evaluated person distance from the vision screening apparatus; based on the evaluated person distance and the Snellen equivalent, determine an adjusted optotype size; and display an optotype in the adjusted optotype size.

In another aspect, a method for visual acuity screening with a vision screening apparatus is disclosed. The example method includes determining a refractive error; determining a Snellen equivalent to the refractive error; determining an optotype based on the Snellen equivalent; determining a distance of a person from the vision screening apparatus; and based on the distance of the person from the vision screening apparatus, adjusting a size of the optotype, thereby generating an adjusted optotype; and displaying the adjusted optotype on a display of the vision screening apparatus.

The details of one or more embodiments are set forth in the accompanying drawings and the description below. Other features, objects, and advantages of these embodiments will be apparent from the description, drawings, and claims.

DESCRIPTION OF THE FIGURES

The following figures, which form a part of this application, are illustrative of described technology and are not meant to limit the scope of the claims in any manner.

DETAILED DESCRIPTION

Figure 1:
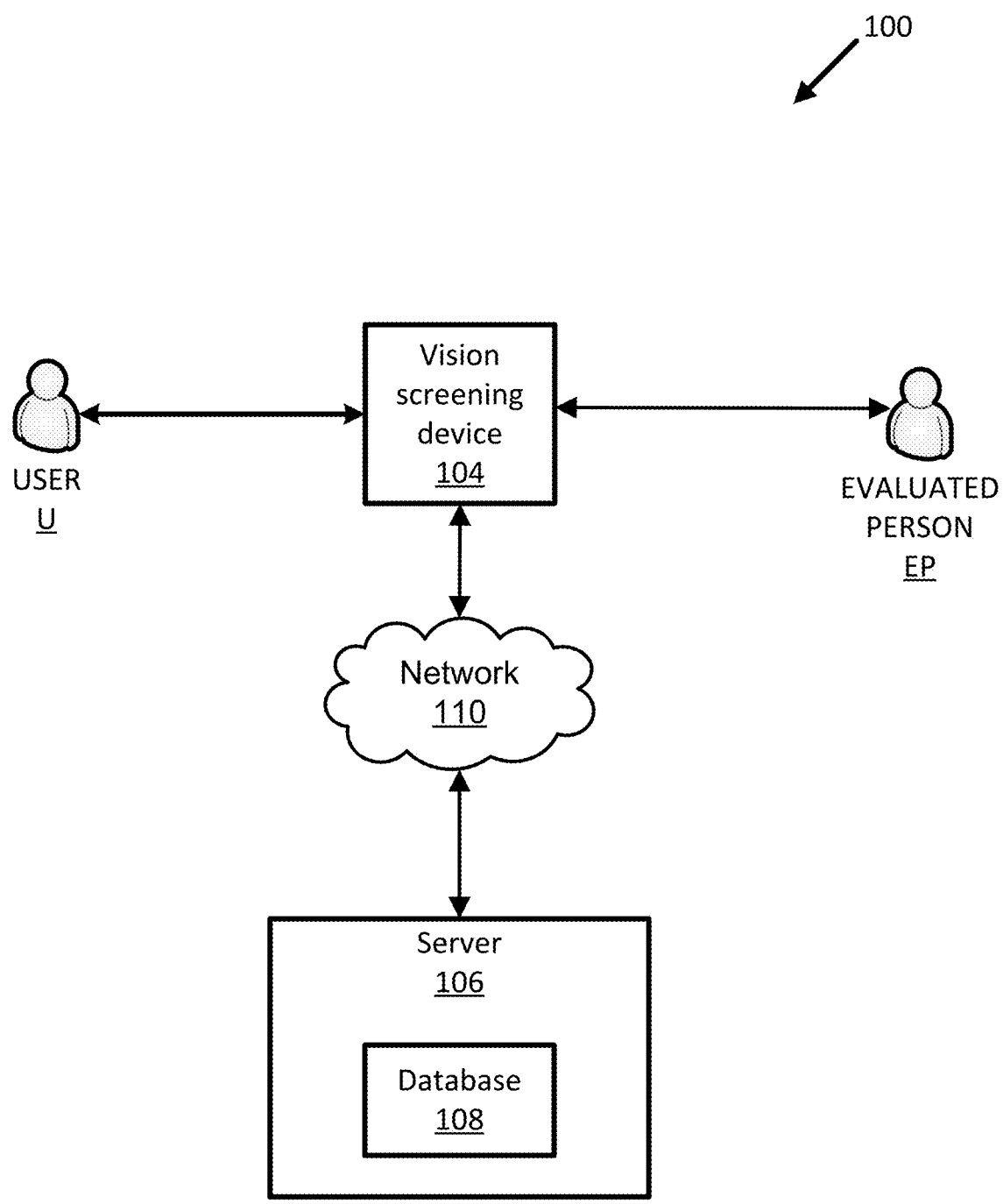
FIG. 1 shows a schematic block diagram of an example visual acuity screening environment.

Various embodiments of the present disclosure will be described in detail with reference to the drawings, wherein like reference numerals represent like parts and assemblies throughout the several views. Additionally, any examples set forth in this specification are not intended to be limiting and merely set forth some of the many possible embodiments.

Visual acuity screening in children and adults has various purposes. For instance, a person's visual acuity can be used to determine treatment and/or correction. Typical visual acuity testing relies on a person reading characters printed on a Snellen chart at a given distance. That person's visual acuity is based on which size of characters on the chart the person can discern. The test usually begins with the person reading the top-most, largest character while covering one eye. Then the person proceeds to read each character in each line until they are no longer able to discern the characters. The process repeats for the opposite eye. A person with "normal vision" of 20/20 will read about 30 characters on the Snellen chart for each test.

In some instances, a large number of people undergo visual acuity screening in a given time frame. For example, a group of kindergarten students at a public school may be screened during a class period. Usually, each kindergarten student waits their turn to be screened, then each student reads up to 30 characters for each eye. This is a time consuming undertaking, which can test the limits of the children's patience.

Broadly, the systems and methods disclosed and contemplated herein are directed towards improving visual acuity testing. Rather than having an evaluated person read 30 characters for each eye, systems and methods disclosed and contemplated herein first show optotypes corresponding to an estimated visual acuity. Thereby, time is not wasted asking the evaluated person to recite lines and characters they can easily read or not read.

FIG. 1 is a schematic block diagram of an example visual acuity screening environment 100. The example visual acuity screening environment 100 includes vision screening device 104, server 106, and database 108. Vision screening device 104 and server 106 are in communication via network 110. In typical operation, user U operates vision screening device 104 to test an evaluated person EP. Other embodiments can include more or fewer components. For example, in any of the embodiments described herein, one or more of the refractive error determinations, Snellen equivalent determinations, or other determinations may be made by a processor or other controller of the screening device 104. In such embodiments, such determinations may be made by the processor or controller of the screening device 104 alone or at least partly in conjunction with the server 106.

Vision screening device 104 is a portable device configured to perform a visual acuity test on the evaluated person EP. Although common environments include schools and portable or permanent medical clinics, because vision screening device 104 is portable, it can be used virtually anywhere the user U takes the vision screening device 104.

Vision screening device 104 is capable of performing both refractive error testing and facilitating visual acuity testing. At a broad level, refractive error testing includes displaying stimuli, detecting pupils, acquiring images of the pupils, and analyzing pupil image data to generate refractive error results. At a broad level, visual acuity testing includes determining an optotype, determining a distance of the evaluated person EP from the vision screening device 104, and displaying a dynamic optotype.

In some examples, vision screening device 104 may communicate with server 106. For example, vision screening device 104 may determine the refractive error results based on the analysis of pupil image data as noted above. Such results may also be determined by the vision screening device 104 based at least in part on demographics, sphere, cylinder, axis, pupillometry and/or other characteristics of the EP. In still further examples, such results may be determined by the vision screening device 104 based at least partly on the accommodation range, binocular gaze deviation, pupillary reaction to the "brightness" of the fixation target, and pre-existing eye or neurological conditions. Objective visual acuity data, such as optic kinetic nystagmus (OKN) data can also be used. In some instances, the server 106 may have access to one or more of these data, for example, by communicating with the database 108 and/or with an electronic health record/electronic medical record database. In such examples, the server 106 may provide such information to the vision screening device 104 such that the vision screening device 104 can determine the refractive error of the EP based at least in part on such data. Additionally or alternatively, such information may be stored locally within a memory associated with and/or in communication with the vision screening device 104. The vision screening device 104 may transmit refractive error testing results to the server 106 via network 110. Server 106, usually in combination with database 108, determines corresponding acuity data based on the refractive error data received from vision screening device 104. Then server 106 transmits the corresponding acuity data to vision screening device 104. In turn, vision screening device 104 uses the corresponding acuity data to provide a visual acuity test for the evaluated person EP.

In alternative implementations, vision screening device 104 determines corresponding acuity data based on the refractive error data. In those implementations, vision screening device 104 may communicate with server 106 to check for updates to any correspondence data or algorithms but otherwise does not rely on server 106 and/or database 108 for determining refractive error or corresponding acuity data. Vision screening device 104 and methods of using vision screening device 104 are described in greater detail below.

Vision screening device 104 includes computing device 801, shown and described below with reference to FIG. 11. In some instances, vision screening device 104 can be in communication with user U-specific devices, such as mobile phones, tablet computers, laptop computers, etc., to deliver or communicate results to those devices.

Server 106 communicates with vision screening device 104 to respond to queries, receive data, and communicate with database 108. Communication from vision screening device 104 occurs via network 110, where the communication can include requests for corresponding acuity data. Server 106 can act on these requests from vision screening device 104, determine one or more responses to those queries, and respond back to vision screening device 104. Server 106 can access database 108 to complete transactions by a vision screening device 104. Server 106 includes one or more computing devices 801, shown and described below with reference to FIG. 11.

Database 108 can be one or more database systems accessible by server 106 storing different types of information. For instance, database 108 can store correlations and algorithms used to determine Snellen equivalents based on refractive error testing. Database 108 can also include clinical data. Database 108 may reside on server 106 or on separate computing device(s) accessible by server 106.

Network 110 is typically any type of wireless network or other communication network known in the art. Examples of network 110 include the Internet, an intranet, a wide area network (WAN), a local area network (LAN), and a virtual private network (VPN), cellular network connections and connections made using protocols such as 802.11a, b, g, n and/or ac.

U.S. application Ser. No. 13/399,682, filed Feb. 17, 2012, describes systems and methods for photorefraction ocular screening and that disclosure is hereby incorporated by reference in its entirety. Example configurations of vision screening device 104, and methods for its use, are shown and described with reference to FIGS. 2-7, below.

Figure 2:
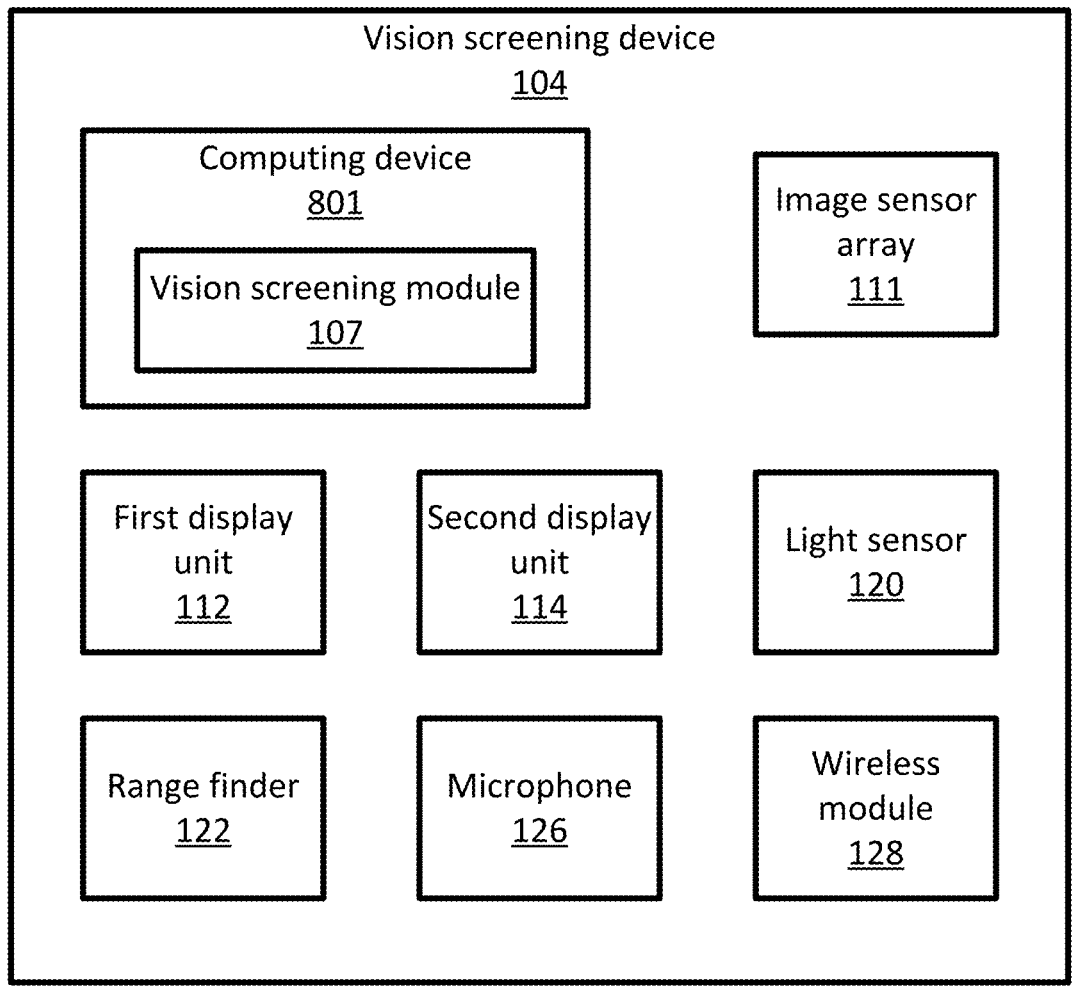
FIG. 2 shows a schematic block diagram of components of a vision screening device used in the visual acuity screening environment of FIG. 1.

FIG. 2 is a schematic block diagram illustrating components of example vision screening device 104. Example vision screening device 104 includes computing unit 801 with vision screening module 107, image sensor array 111, first display unit 112, second display unit 114, a light sensor 120, a range finder 122, a microphone 126, and a wireless module 128. The second display unit 114 is oriented to face the user U and the first display unit 112 is oriented to face the evaluated person EP. Other embodiments can include more or fewer components.

Figure 7:
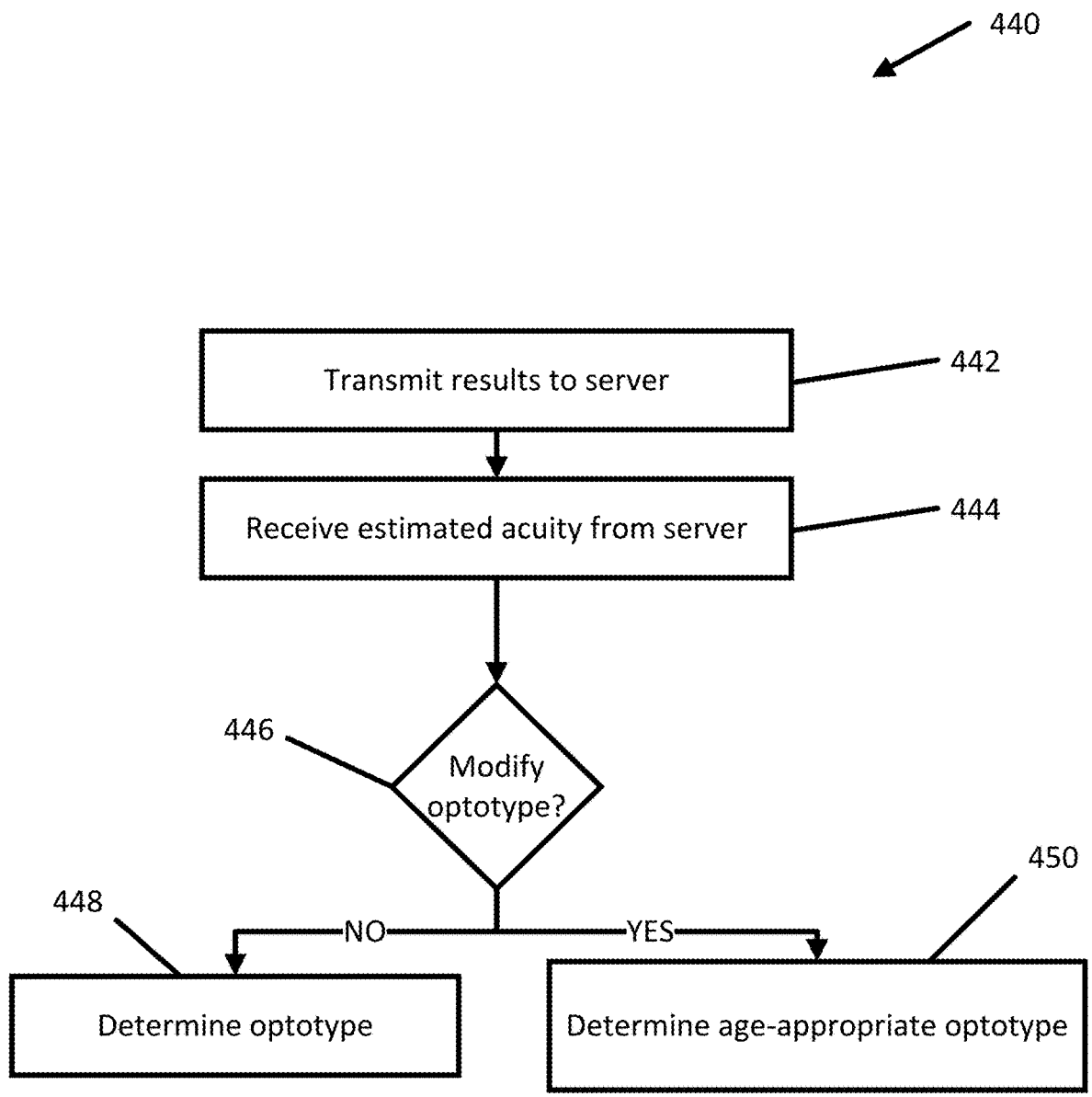
FIG. 7 shows an example method for determining a modified optotype in the method shown in FIG. 5.

Computing unit 801 is in communication with the components of vision screening device 104, including image sensor array 111, first display unit 112, second display unit 114, light sensor 120, range finder 122, microphone 126, and wireless module 128. In embodiments where the lens is adjustable, the computing unit 801 is also in communication with a device, such as a mechanical motor, that adjusts the position of the lens. Components of example computing unit 801 are shown in FIG. 7 and described below.

Vision screening module 107 includes, for example, instructions for displaying a refractive error result on the first display unit 112, for processing the images received on the image sensor array 111, and for guiding and informing the user U about optotype display and test results for the evaluated person EP. Optotypes include, for example, letters, shapes, objects, and numbers.

Image sensor array 111 receives light and conveys image data to computing unit 801. The image sensor array 111 is, for example, a complementary metal-oxide semiconductor (CMOS) sensor array, also known as an active pixel sensor (APS), or a charge coupled device (CCD) sensor. In some embodiments, a lens is supported by the vision screening device 104 and positioned in front of the image sensor array 111.

Image sensor array 111 has a plurality of rows of pixels and a plurality of columns of pixels. In some embodiments, the image sensor array 111 has about 1280 by 1024 pixels, about 640 by 480 pixels, about 1500 by 1152 pixels, about 2048 by 1536 pixels, or about 2560 by 1920 pixels. The image sensor array 111 is capable of capturing about 25 frames per second (fps); about 30 fps; about 35 fps; about 40 fps; about 50 fps; about 75 fps; about 100 fps; about 150 fps; about 200 fps; about 225 fps; or about 250 fps. It is understood that the above pixel counts are merely examples, and in additional embodiments the image sensor array 111 may have a plurality of rows including greater than or less than the number of pixels noted above. Additionally, the image sensor array 112 may have a plurality of columns including greater than or less than the number of pixels noted above.

Image sensor array 111 includes photodiodes that have a light-receiving surface and have substantially uniform length and width. During exposure, the photodiodes convert the incident light to a charge. The image sensor array 111 can be operated as a global shutter, that is, substantially all of the photodiodes are exposed simultaneously and for substantially identical lengths of time. Alternatively, the image sensor array 111 is used with a rolling shutter mechanism, in which exposures move as a wave from one side of an image to the other. Other mechanisms are possible to operate the image sensor array 111 in yet other embodiments. Image sensor array 111 is capable of capturing digital images. The digital images can be captured in various formats, such as JPEG, BITMAP, TIFF, PGM, PGV, etc.

First display unit 112 conveys information to user U about the positioning of the vision screening device 104 as well as test results. First display unit 112 is, for example, a liquid crystal display (LCD) or active matrix organic light emitting display (AMOLED). First display unit 112 can be touch-sensitive to receive input from the user U.

Information provided to the user U on first display unit 112 includes, for example, the evaluated person's EP distance from the vision screening device 104, the quality of the focus, the progress of the evaluation, the results of the evaluation, and options for transmitting the results to another database.

Second display unit 114 displays one or more visual tests to the evaluated person EP. In one implementation, second display unit 114 is a display, such as a liquid crystal display (LCD) or an active matrix organic light emitting display (AMOLED). Second display unit 114 can also include a light-emitting diode (LED) array having visible LEDs and near-infrared LEDs. In some implementations, a beam splitter directs the light emitted from the LED array towards the evaluated person. The second display unit 114 is in communication with computing unit 801.

The near-infrared LEDs in the LED array have a wavelength of about 850 nanometers (nm) and are used in capturing pupil images. Generally, the visible LEDs in the LED array have a wavelength of less than about 630 nm. This configuration allows for visual stimulus to be shown to the evaluated person EP, but not seen in the images captured by the image sensor array 111. In some embodiments, the visible LEDs are positioned between, and co-planar with, the near-infrared LEDs in the LED array.

In some embodiments, amber LEDs are among the visible LEDs used in second display unit 114. In addition to the procedures described herein, such LEDs may have utility in a variety of different examination procedures including, among other things, examinations related to eye tracking and/or concussion protocols. Amber LEDs have a wavelength of about 608 nm to about 628 nm. The computing unit 801 can regulate the amount of power directed to the LEDs in the LED array. In order to minimize the evaluated person's EP pupil constriction and eye strain, the amber LEDs are illuminated at low to medium power. For example, a 20 mA LED can be run at between about 2 mA to about 10 mA. Alternatively, low brightness amber LEDs can be used, for example, LEDs that run at about 0.5 mA. Additionally, LEDs can be pulse modulated. Visible light LEDs in colors other than amber, when present in the second display unit 114, can also be operated at low to medium power. Further, in some examples the vision screening device 104 may include one or more diffusers disposed in an optical path of one or more LEDs in the LED array. For example, such a diffuser may comprise a window, lens, prism, filter, and/or other substantially transparent optical component configured to at least partly diffuse radiation emitted by the one or more LEDs. As a result, for example, light emitted by the one or more LEDs may not appear to be as bright when observed by the evaluated person EP. In some such examples, diffusing light emitted by one or more of the LEDs in this way may reduce an amount of accommodation by the evaluated person EP and, as a result, the improve the accuracy of the refractive error measurement made by the vision screening device 104. Thus, the accuracy of Snellen equivalent determinations made based on such refractive error measurements may also be improved.

Vision screening device 104 can record the details of each test environment. For example, light sensor 120 of vision screening device 104 may record the quantity of ambient light, time of day, ambient noise level, etc. These data can additionally be used to, for example, evaluate refractive error testing. For example, an expected pupil size of the evaluated person EP may be determined by the vision screening device 104 based at least partly on a relationship between pupil diameter and the quantity of ambient light. Thus, if an evaluated person's EP pupils are inappropriate for a given amount of ambient light, the vision screening device 104 may determine, based at least partly on such information, that the evaluated person EP is having a strong accommodative response under such conditions and may utilize this information in determining more accurate refractive error testing results. Thus, the accuracy of Snellen equivalent determinations made based on such refractive error measurements may also be improved.

Light sensor 120 detects the ambient light intensity around the vision screening device 104. Above certain brightness thresholds, the evaluated person's EP pupils constrict to the point where the diameter of the pupil is so small that the vision screening device 104 may not be configured to determine the refractive error of the evaluated person EP accurately. If computing unit 801, in combination with light sensor 120, determines the ambient light is too bright, second display unit 114 communicates to the user U or evaluated person EP to use a light block or move to an environment with less ambient light. In some examples, the computing device 801 may also be configured to adjust and/or otherwise control the brightness, sharpness, contrast, and/or other operational characteristic of the second display unit 114 based at least in part on one or more signals received from the light sensor 120. For example, based at least in part on the ambient light intensity measured by the light sensor 120, the computing device 801 may be configured to adjust (e.g., automatically, dynamically, and/or in real time) the brightness, backlight, and/or other parameters of the second display unit 114 in order to maintain the contrast ratio at a desired level or within a desired range.

In some examples, the image sensor array 111 and/or other components of the vision screening device 104 may perform one or more of the same functions (either alone or in combination with the light sensor 120) described above with respect to the light sensor 120. In particular, in some examples the image sensor array 111 may capture an initial image of the ambient surroundings. The computing unit 801 may then determine, based at least in part on the captured image, whether there is too much ambient or IR light to perform one or more of the photorefracting operations described herein. If so, the computing unit 801 may control the second display unit 114 to instruct the user U or evaluated person EP to use a light block, or move to an environment with less ambient light.

For example, in some embodiments the image sensor array 111 and/or the vision screening device 104, generally, may be configured to tolerate up to a threshold level of ambient IR light. In such examples, too much IR light from incandescent bulbs or sunlight may cause pupil images to be over exposed and washed out. Too much ambient visible light, by contrast, may cause the evaluated person's EP pupils to be too small to measure with accuracy. In such examples, the image sensor array 111 and/or the vision screening device 104, generally, may be configured to sense both ambient visible and IR light, and to inform the user U as to visible and IR light levels that may be above respective thresholds. In such examples, a photodiode could be used to sense the overall level of ambient light, and an image captured by the image sensor array 111 with all the IR LED's turned off could be used as a measure of ambient IR light.

Range finder 122, in combination with computing unit 801, determines a distance of the evaluated person EP from the vision screening device 104. In some embodiments, range finder 122 is an infrared transceiver unit, an ultrasonic transceiver unit, or another distance measuring unit known to one of skill in the art.

Generally, the evaluated person EP is positioned about 1 meter (m), 10 feet, or 20 feet from the vision screening device 104. Other distances are possible, such as 16 inches, 20 inches, 30 inches, 35 inches, 40 inches, and 45 inches away. It is understood that the distances listed above are merely examples, and in additional embodiments, distances greater than or less than those noted above may be used during a visual acuity test and/or other tests described herein. The vision screening device 104 provides guidance to the evaluated person EP and/or the user U about how to adjust the relative positioning between the vision screening device 104 and the evaluated person EP to obtain a focal distance that will yield functional images. In embodiments where a user U operates the vision screening device 104, the guidance is displayed on first display unit 112. For example, first display unit 112 can instruct the user U that the evaluated person EP is too close, too far away, or within a proper distance.

In some embodiments, the focal length is about, 0.2 m, about 0.3 m, about 0.4 m, 0.5 m, about 0.6 m, about 0.7 m, about 0.75 m, about 0.8 m, about 0.9 m, about 1.0 m.

Microphone 126 receives responses spoken by evaluated person EP. In embodiments, the evaluated person EP speaks as part of the visual acuity test. For example, the evaluated person EP is asked to read an optotype, such as a letter, shown on the second display unit 114 and microphone 126 receives the evaluated person's EP responses. Then computing unit 801, in combination with voice recognition software, decodes the responses and uses the decoded responses in the visual acuity determination. Additionally or alternatively, the user U may record the evaluated person's EP responses manually and/or by interacting with one or more data input/touch input fields presented on the first display unit 112.

Wireless module 128 can connect to external databases to receive and send refractive error and/or visual acuity test data using wireless connections. Wireless connections can include cellular network connections and connections made using protocols such as 802.11a, b, g, and/or ac. In other examples, a wireless connection can be accomplished directly between the vision screening device 104 and an external display using one or more wired or wireless protocols, such as Bluetooth, Wi-Fi Direct, radio-frequency identification (RFID), or Zigbee. Other configurations are possible.

The communication of data to an external database can enable report printing or further assessment of the evaluated person's test data. For example, data collected and corresponding test results are wirelessly transmitted and stored in a remote database accessible by authorized medical professionals.

Figure 3:
FIG. 3 is a front, left perspective view of an embodiment of a vision screening device used in the visual acuity screening environment of FIG. 1.
Figure 4:
FIG. 4 is a rear plan view of the embodiment of the vision screening device shown in FIG. 3.

FIGS. 3 and 4 show an example embodiment of vision screening device 200. FIG. 3 is a front-left perspective view, and FIG. 4 is a rear-plan view. Example vision screening device 200 includes some or all components described above with reference to vision screening device 104. Example vision screening device 200 includes housing 202, first display unit 204, second display unit 206, and range finder 208. A commercial embodiment of example vision screening device 200 is the Spot™ Vision Screener VS100 by Welch Allyn® (Skaneateles Falls, N.Y.). Other embodiments can include more or fewer components.

Housing 202 provides support for components of vision screening device 200 as well as one or more aspects configured to facilitate hand-held operation. In some instances, example vision screening device 200 can also be mounted on a surface, such as a tripod. First display unit 204 typically faces a user operating vision screening device 200 such that the user can navigate various control interfaces and view test results. Although shown oriented at an angle relative to a user, first display unit 204 can have other orientations in different embodiments.

Second display unit 206 is positioned on an opposite end of the housing 202 such that second display unit 206 faces the evaluated person during typical operation. Second display unit 206 can include, as mentioned above, a display and one or more LEDs or LED arrays. An image sensor array is positioned on the interior of housing 202 and behind the second display unit 206, or adjacent thereto. In one implementation, light traveling from the evaluated person's pupils passes through second display unit 206 where the light is received by image sensor array. Alternatively, an image sensor array is positioned adjacent to second display unit 206 (e.g., below or above the second display unit 206) such that light need not pass through second display unit 206 to reach image sensor array devices. In still further examples, the second display unit 206 may be disposed orthogonal to the image sensor array. In such examples, the second display unit 206 may be configured to project an image onto a window, mirror, lens, or other substantially transparent substrate through which the image sensor array may capture one or more images.

Range finder 208 determines a distance from vision screening device 200 to the evaluated person. More particularly, range finder 208 determines the distance from the evaluated person's face to the second display unit 206. As discussed elsewhere herein, range finder 208 can determine a distance of an evaluated person at the beginning of a test and/or dynamically determine the evaluated person distance throughout the various tests.

Figure 5:
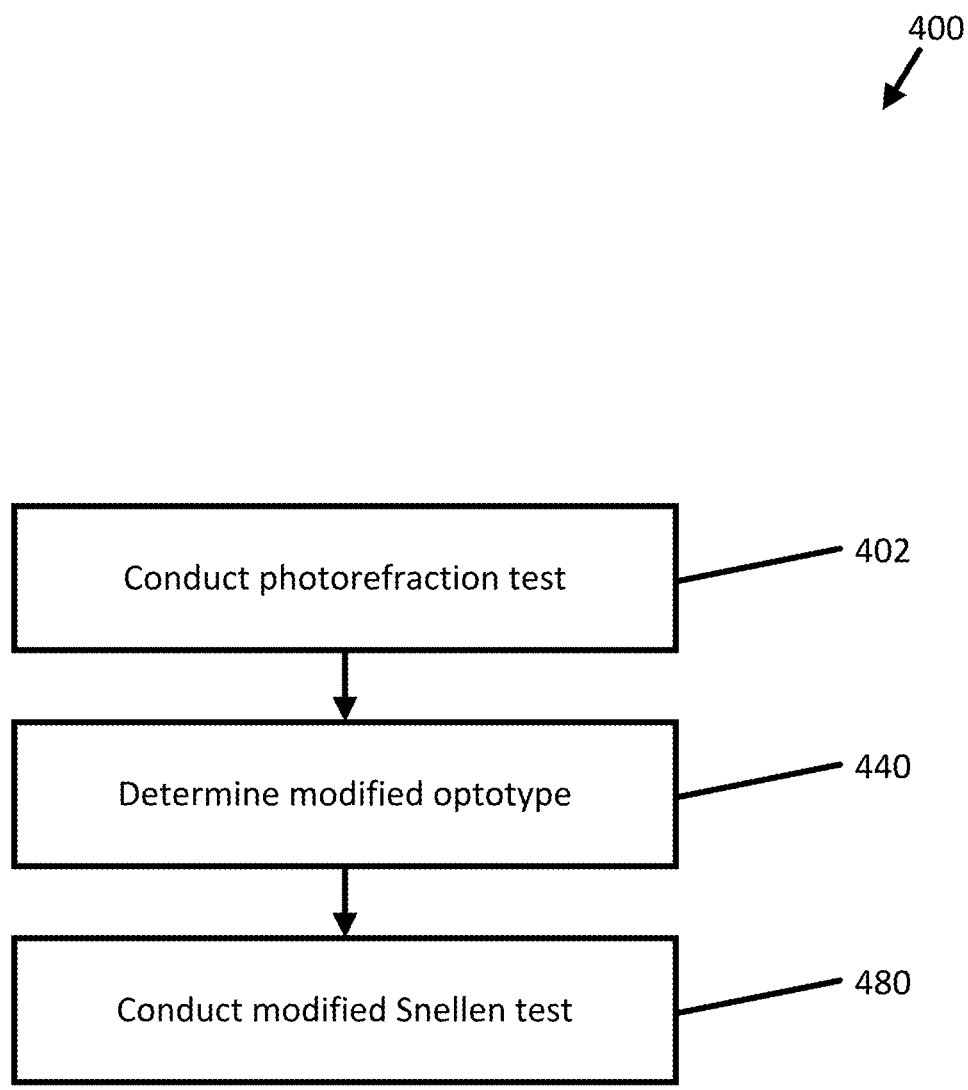
FIG. 5 shows an example method for visual acuity screening with a vision screening device.

FIG. 5 shows an example method 400 for visual acuity screening with a vision screening device. Broadly, example method 400 includes conducting a photorefraction ocular screening test (operation 402), determining a modified optotype (operation 404), and conducting a modified Snellen test (operation 440). The example vision screening devices disclosed herein can be used to conduct example method 400. Other embodiments can include more or fewer operations. It is understood that the one or more Snellen tests described herein are merely examples of visual acuity examinations utilizing specific optotypes. In further embodiments, the systems, devices, and/or methods described herein may supporting several different optotypes to cover different regional preferences including but not limited to Snellen, LogMar, Tumbling E, Landolt C, and Lea Symbols. Accordingly, any of the visual acuity examinations described herein may comprise optotype tests that may generate a visual acuity test result in the format of 20/20, 20/30, and so on.

Example method 400 begins by conducting a photorefraction ocular screening test (operation 402). The photorefraction ocular screening test obtains one or more parameters regarding an evaluated person's vision, eyesight, and physical traits and generates refractive error results. The refractive error results of the photorefraction ocular screening test (operation 402) are used to determine modified optotypes for one or more subsequent Snellen tests.

Figure 6:
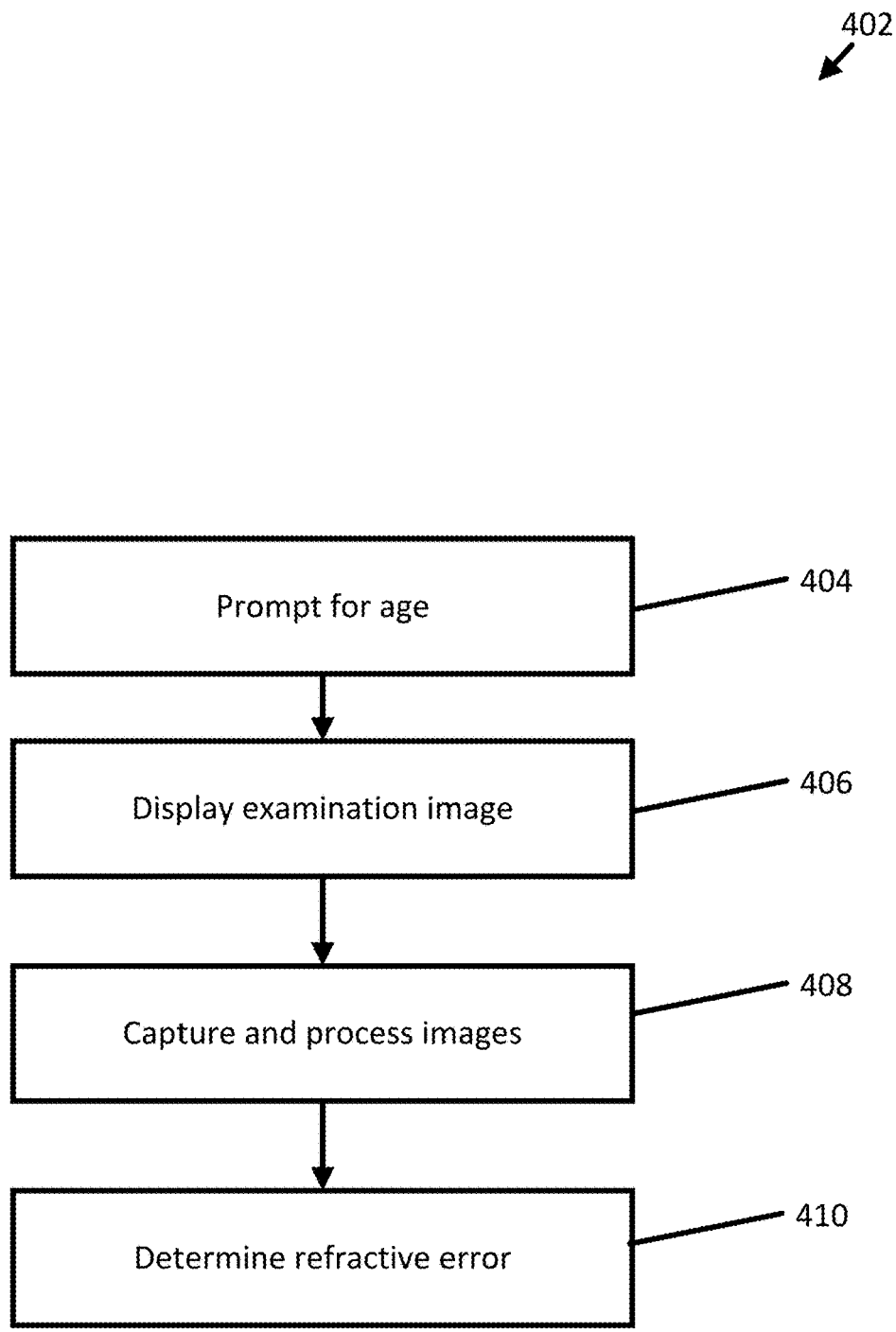
FIG. 6 show an example method for conducting a photorefraction ocular screening test in the method shown in FIG. 5.

Referring to FIG. 6, conducting photorefraction ocular screening test (operation 402) includes prompting for an age (operation 404). Here, a person operating the vision screening device enters the age of the person being evaluated. Typically, a first display unit of the vision screening device is touch sensitive or voice operated, thereby enabling the user to enter in the age of the evaluated person.

Next, an examination image is displayed (operation 406). Examination images displayed during operation 406 can be fixation targets, objects, letters, etc., and may include one or more of the aforementioned types. Example examination images, and processes for displaying them, are described in U.S. patent application Ser. No. 13/399,682, noted above as incorporated by reference in its entirety.

During the display of one or more examination images (operation 406), vision screening device captures and processes images of the evaluated person's pupils (operation 408). Example image processing, including capturing and processing pupillometry images, is described in U.S. patent application Ser. No. 13/399,682, noted above as incorporated by reference in its entirety.

After capturing one or more images and processing them (operation 408), a refractive error is determined (operation 410). Refractive error can be a single parameter describing characteristics of the evaluated person's vision. More preferably, refractive error includes more than one parameters relating to vision and physical characteristics of the evaluated person. For example, refractive error can include data regarding spherical equipment, sphere, cylinder, axis, gaze angle, pupil diameter, and inter-pupillary distance of the evaluated person.

Referring now to FIG. 7, determining a modified optotype (operation 440) is shown. As noted above, in some examples, any of the calculations, operations, and/or determinations associated with determining refractive error and/or a Snellen equivalent may be performed locally on the vision screening device 104 with or without assistance from or communication with the server 106. For discussion purposes, however, FIG. 7 will be described according to an embodiment in which information is transmitted between the vision screening device 104 and the server 106, and in which the server 106 determines a Snellen equivalent based at least partly on refractive error test results determined by the vision screening device 104. First, refractive error results may be transmitted to the server 106 (operation 442) via a wireless connection. In some instances refractive error result data are transmitted in their raw form and the server 106 processes the raw data. Alternatively, the transmission includes processed data indicating values for one or more parameters resulting from processing the refractive error test data. In some examples, transmissions to the server 106 may include a request for an estimated acuity from the server.

Next, the vision screening device 104 may receive estimated acuity data from the server 106 (operation 444). Estimated acuity data includes a Snellen equivalent, determined based on an evaluation of the refractive error data. Examples Snellen equivalents include 20/20, 20/40, 20/80, and the like. In some examples, such Snellen equivalents may also be provided based on a distance between the evaluated person EP and the testing device equal to 10 feet. In such examples, such Snellen equivalents may include 10/10, 10/20, 10/30, 10/40, and the like. In still further examples, such Snellen equivalents may be provided based on a distance between the evaluated person and the testing device equal to 6 meters. In such examples, such Snellen equivalents may include 6/6, 6/12, 6/24, and the like. In any of the examples described herein, the user U may select (e.g., via a set-up screen of the vision screening device 104 and/or in real time during an acuity test performed using the vision screening device 104) one or more of the above formats for the purposes of displaying results of the various visual acuity examinations. For example, the user U may select a country and/or a geographic region (e.g., U.S., North America, South America, Europe, China, Japan, etc.) in which the vision screening device 104 is being used, and the vision screening device 104 may display and/or otherwise output Snellen equivalents and/or visual acuity test results formatted in a manner corresponding to the norms (e.g., metric units, standard units, etc.) of the selected country and/or geographic region. Such a selection may be made via one or more controls, user interface components, or other components of the vision screening device 104.

Then a determination is made whether to modify the optotype (decision 446). Whether to modify the optotype (decision 446) is typically made based on the age of the evaluated person. Depending on the implementation, various age groups can have specific optotypes. Age-appropriate optotypes are characters many children of a given age are able to recognize. For example, children that are not old enough to read or recognize letters of the alphabet may be shown optotypes comprising one or more shapes (e.g., triangle, square, circle, etc.), recognizable images (a tree, a house, a dog, etc.) or other items that the child may be able to positively identify. Children that are old enough to read and/or recognize letters, on the other hand, may be presented with standard Snellen optotypes. Example age groups include 1 to 2 years old, 2 to 5 years old, 5 to 7 years old, and over 7 years old. In another implementation, any evaluated person having an age less than a predetermined age, such as 6 years old, is provided with a modified optotype. Other age ranges and thresholds are contemplated. Further, in any of the examples described herein, the user U may select (e.g., via a set-up screen of the vision screening device 104 and/or in real time during an acuity test performed using the vision screening device 104) one or more of the above optotype formats. For example, if a child is struggling to read letters as part of a standard Snellen-type acuity examination, the user U may select an alternative optotype protocol or format (e.g., a shape-based or image-based series of optotypes), in real-time (e.g., during the examination) in order to complete the acuity examination with the child. Such a selection may be made via one or more controls, user interface components, or other components of the vision screening device 104.

If the optotype does not have to be modified, then an optotype corresponding to the estimated acuity is determined (operation 448). In most instances, an optotype that has not been modified is a letter.

If the optotype does need to be modified, then an age-appropriate optotype is determined (operation 450). As discussed above, determining an age appropriate optotype includes determining a group or sub-group of the evaluated person. Based on the age, group, or sub-group, an appropriate optotype is determined. For example, for children under the age of 5, an object or shape may be age appropriate. In any of the examples described herein, the user U may also select a country-appropriate and/or geographic region-appropriate optotype format for providing during an acuity examination. For example, the user U may select a country and/or a geographic region (e.g., U.S., North America, South America, Europe, China, Japan, etc.) in which the vision screening device 104 is being used. Additionally or alternatively, the user U may select a language with which the examined person EP is conversant (e.g., English, Chinese, Russian, Japanese, etc.). In such examples, the vision screening device 104 may display and/or otherwise output optotypes corresponding to the norms of the selected country and/or geographic region. In particular, the vision screening device 104 may display characters in the selected language and/or in a language that is generally spoken in the selected country or geographic region. Such a selection may be made via one or more controls, user interface components, or other components of the vision screening device 104.

Figure 8:
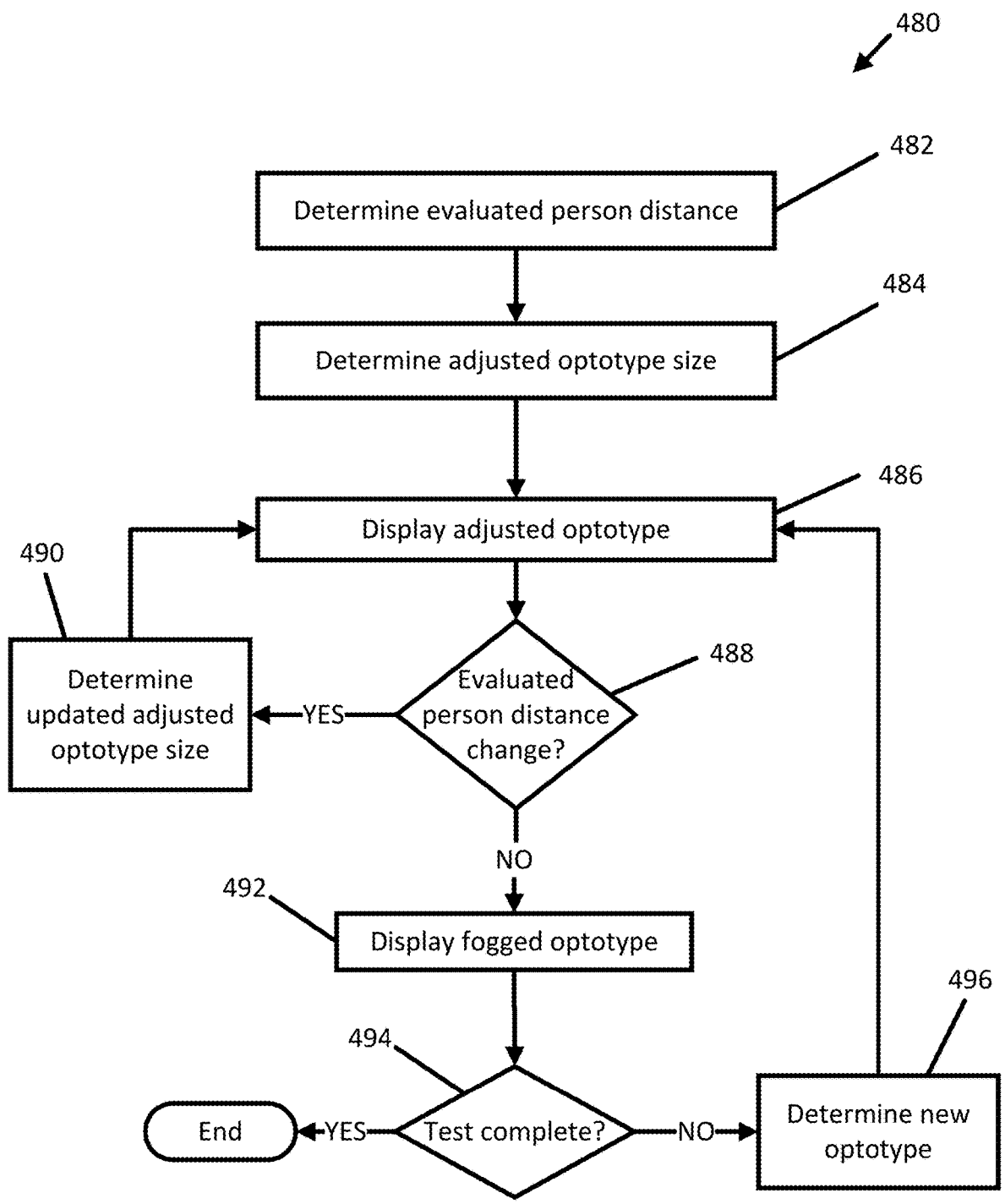
FIG. 8 shows an example method for conducting a modified Snellen test in the method shown in FIG. 5.

Referring now to FIG. 8, conducting a modified Snellen test (operation 480) is shown. First, an evaluated person distance is determined (operation 482). The evaluated person distance is the distance from the person to the vision screening device. More particularly, the evaluated person distance is a distance from the person's pupils, roughly, to the second display unit of the vision screening device. Effectively, the evaluated person distance is the distance between the person's pupils and the optotype displayed on the vision screening device.

Based on the evaluated person distance, an adjusted optotype size (operation 484) is determined. Typical Snellen chart-based vision acuity tests position the evaluated person at a set distance from the chart. For example, an evaluated person is positioned six meters from the chart. Using six meters as a baseline, then, the optotype is adjusted to be bigger or smaller based on how far the person is from the vision screening device.

As an example, the evaluated person is positioned two meters from the vision screening device. There, the optotype corresponding to the Snellen equivalent is decreased in size such that the ratio of the optotype at a distance of six meters is the same as the optotype at the evaluated person distance from the vision screening device, which is two meters. In such examples, the vision screening device 104 may dynamically (e.g., in real time) adjust the size of the optotype based at least in part on the distance between the evaluated person EP and the vision screening device 104.

After determining an adjusted optotype size (operation 484), the adjusted optotype is displayed (operation 486) on the second display unit of the vision screening device. The optotype is also displayed on the first display unit so that the user can verify whether the evaluated person correctly identifies the optotype. At this moment, the user evaluating the evaluated person usually questions the evaluated person about what is shown on the display. Alternatively, an audible prompt can be emitted by the vision screening device asking the evaluated person what the optotype is.

In some implementations, the evaluated person distance is continually monitored until the test is complete (operation 488). Test completion can be indicated by a user or by the vision screening device receiving a correct response from the evaluated person. If the evaluated person distance changes, then an updated adjusted optotype size (operation 490) is determined. As an example, if the person moves closer to the vision screening device, then the adjusted optotype becomes smaller to compensate for the closer focal distance between the evaluated person and the vision screening device. Size changes in the optotype correspond to changes in the evaluated person distance.

It is understood that an evaluated person EP that is hyperopic may perform well on a Snellen-type visual acuity evaluation when the evaluated person EP is at a standard distance (e.g., 6 meters, 10 feet, 20 feet) from the vision screening device 104. However, this same evaluated person EP may not perform well on (e.g., may fail) a Snellen-type visual acuity examination when the evaluated person EP is relatively close to the vision screening device 104 (e.g., 16 inches, 24 inches, etc.). Thus, in some examples, in addition to displaying the optotype at a relatively standard distance (e.g., 6 meters, 10 feet, 20 feet) (operation 486), the method 480 shown in FIG. 8 may also include the steps of providing a visual, audible, or other instruction to the user U to change the distance between the evaluated person EP and the vision screening device 104. In particular, the first display unit 112 may display distances, instructions, and/or other information to the user U in order to assist the user in placing the vision screening device 104 relatively close to the evaluated person (e.g., a distance of 16 inches, 24 inches, etc.). Once the desired distance is reached, the second display unit 114 may display one or more appropriately sized optotypes to the evaluated person EP, and the acuity test may be performed at relatively close range. Such example operations may be useful in, for example, identifying hyperopic subjects that would normally pass a Snellen test at standard distances. Additionally, testing the evaluated person at the relatively short distances noted above first, and then testing the evaluated person EP at relatively standard distances may assist in identifying myopic patients that may normally pass a Snellen test at close range.

In some instances, a fogged optotype is displayed (operation 492) in addition to, or in place of, the adjusted optotype. Generally, displaying a fogged optotype is a way to double-check the Snellen test result. The fogged optotype displayed (operation 492) can be the same optotype, although typically a different optotype is shown as fogged. In some instances the optotype automatically fogs or de-fogs as time progresses. The user may instruct the vision screening device to display a fogged optotype, or a fogged optotype can be automatically shown after the evaluated person correctly identifies the displayed adjusted optotype.

Figure 9A:
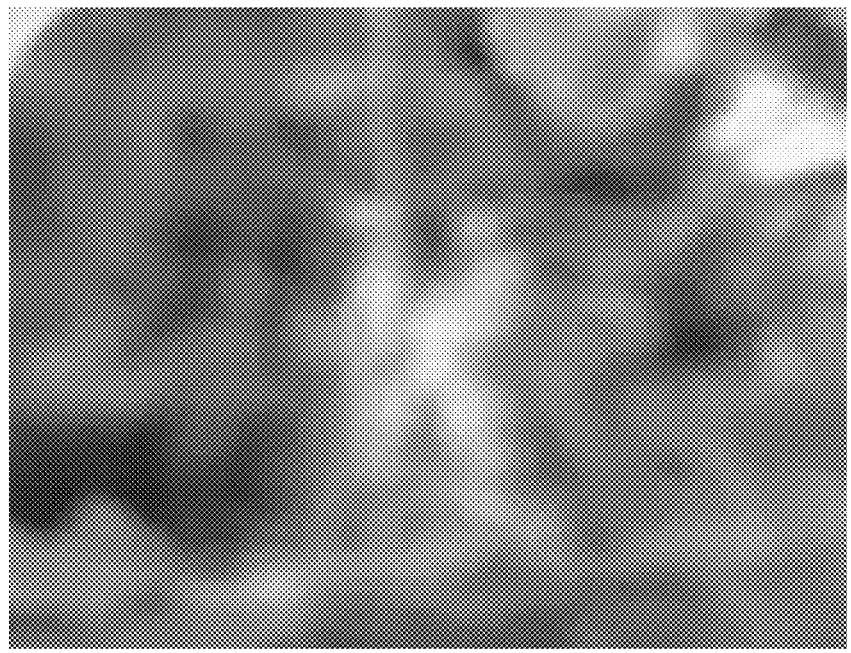
FIG. 9A shows an example embodiment of a fogged optotype.
Figure 9B:
FIG. 9B shows a clear version of the fogged optotype in FIG. 9A.

An example fogged optotype is shown in FIG. 9A. There, the optotype is an object, a bird's nest. However, other defocused/fogged optotypes for letters, shapes, and numbers are possible. For comparison, a clear, non-fogged picture of the image in FIG. 9A is shown in FIG. 9B. In any of the examples described herein, "fogging" an optotype, as shown in FIG. 9A, may reduce the evaluated person's EP ability to accommodate while viewing and/or focusing on the optotype. As a result, a more accurate acuity determination may be made for some evaluated persons EP. For instance, a child that is hyperopic but that is highly accommodating may be able to pass a standard Snellen-type acuity test. However, that same child may struggle to pass an acuity examination with fogged images or other such optotypes that minimize the child's ability to accommodate.

Next, a determination is made whether the test is complete (decision 494). Typically, the user will indicate that the test is complete after the evaluated person correctly identifies the displayed adjusted optotypes and/or the displayed fogged optotype(s).

If, however, the user determines that a new optotype should be displayed, then vision screening device determines a new optotype (operation 496). In some instances, the optotype category may change. For example, if a letter optotype was displayed, and not recognized by the evaluated person, then an object (or number or shape) will be displayed next.

After determining that a new optotype should be displayed, example operation 480 returns either to determine an adjusted optotype size (operation 484) or to display a new optotype in the adjusted optotype size (operation 486). Typically, the process returns a limited number of times, such as once or twice, before ending the test even if the evaluated person has not correctly identified the optotype.

Figure 10:
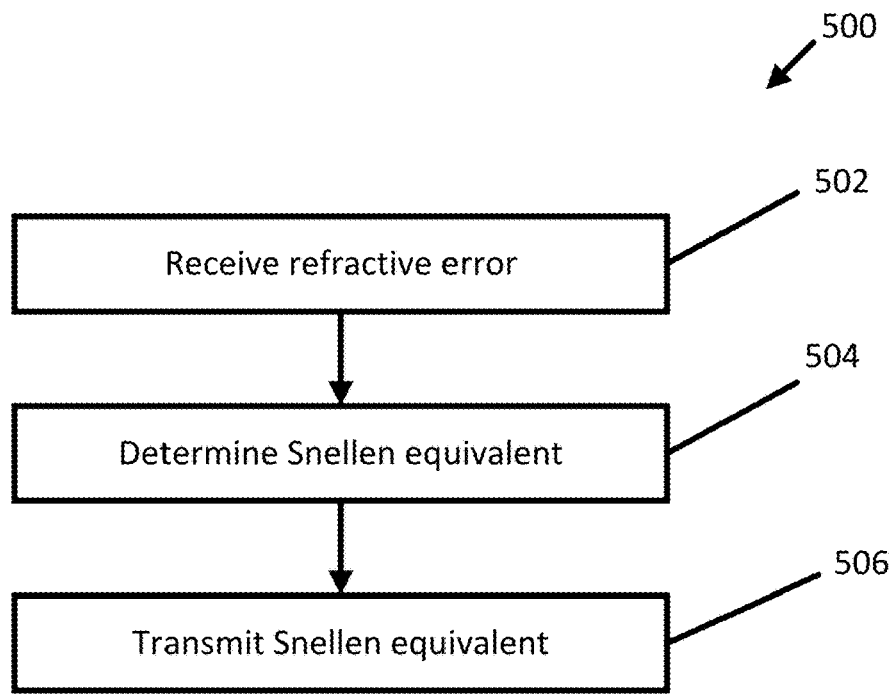
FIG. 10 shows an example method for determining a Snellen equivalent.

FIG. 10 is an example method 500 for determining a Snellen equivalent. Typically, a server device conducts the operations of example method 500. The server device can be in communication with a database. In some instances, a vision screening device conducts some or all of the operations of example method 500. Other embodiments can include more or fewer operations.

Example method 500 begins by receiving refractive error data (operation 502). Refractive error data are included in a communication from a vision screening device. Based on the received refractive error data, a Snellen equivalent is determined (operation 504). The Snellen equivalent can be determined by correlating one or more refractive error parameters with equivalent visual acuity. For instance, one or more of the following parameters is used to identify a Snellen equivalent: spherical equivalent, sphere, cylinder, axis, gaze angle, pupil diameter, demographics (age, gender, ethnicity, etc.), pupil dynamics (e.g., the diameter and/or size of the patient's pupil as a function of time), and/or interpupillary distance. Then, the determined Snellen equivalent is transmitted (operation 506) back to the device that sent the refractive error data.

Figure 11:
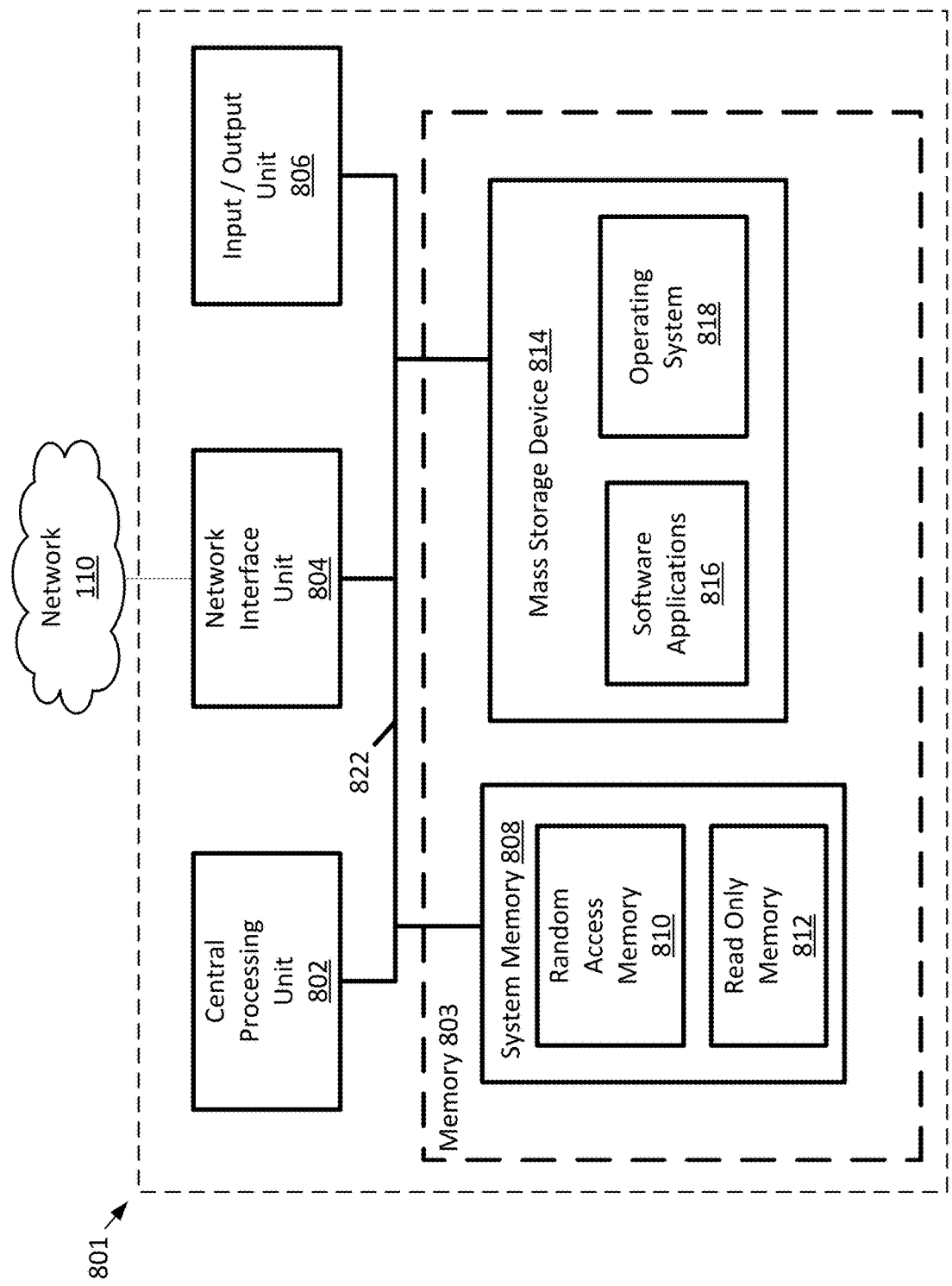
FIG. 11 shows example physical components of a computing device used in the visual acuity screening environment of FIG. 1.

FIG. 11 shows an example computing device 801 hosting software applications 816 configured to perform some or all of the processes discussed and contemplated herein. Some or all components of example computing device 801 are typically used in the computing devices of visual acuity screening environment 100.

As illustrated, the example computing device 801 includes at least one central processing unit ("CPU") 802, memory 803, and a system bus 822 that couples system memory 808 to CPU 802. Memory 803 includes system memory 808 and mass storage device 814. System memory 808 includes random access memory ("RAM") 810 and read-only memory ("ROM") 812. A basic input/output system (BIOS) that contains the basic routines that help to transfer information between elements within the example computing device 801, such as during startup, is stored in the ROM 812. The example computing device 801 further includes mass storage device 814. Mass storage device 814 is able to store software instructions and data.

Mass storage device 814 is connected to CPU 802 through a mass storage controller (not shown) connected to the system bus 822. Mass storage device 814 and its associated computer-readable data storage media provide non-volatile, non-transitory storage for the example computing device 801. Although the description of computer-readable data storage media contained herein refers to a mass storage device, such as a hard disk or solid state disk, it should be appreciated by those skilled in the art that computer-readable data storage media can be any available non-transitory, physical device or article of manufacture from which the central display station can read data and/or instructions.

Computer-readable data storage media include volatile and non-volatile, removable and non-removable media implemented in any method or technology for storage of information such as computer-readable software instructions, data structures, program modules or other data. Example types of computer-readable data storage media include, but are not limited to, RAM, ROM, EPROM, EEPROM, flash memory or other solid state memory technology, CD-ROMs, digital versatile discs ("DVDs"), other optical storage media, magnetic cassettes, magnetic tape, magnetic disk storage or other magnetic storage devices, or any other medium which can be used to store the desired information and which can be accessed by the example computing device 801.

According to various embodiments of the disclosure, the example computing device 801 may operate in a networked environment using logical connections to remote network devices through the network 110, such as a wireless network, the Internet, or another type of network. The example computing device 801 may connect to the network 110 through a network interface unit 804 connected to the system bus 822. It should be appreciated that the network interface unit 804 may also be utilized to connect to other types of networks and remote computing systems. The example computing device 801 also includes an input/output controller 806 for receiving and processing input from a number of other devices, including a touch user interface display screen, or another type of input device. Similarly, the input/output controller 806 may provide output to a touch user interface display screen or other type of output device.

As mentioned briefly above, mass storage device 814 and RAM 810 of the example computing device 801 can store software instructions and data. The software instructions include an operating system 818 suitable for controlling the operation of the example computing device 801. The mass storage device 814 and/or the RAM 810 also store software instructions, that when executed by the CPU 802, cause the example computing device 801 to provide the functionality of the example computing device 801 discussed herein. For example, the mass storage device 814 and/or the RAM 810 can store software instructions that, when executed by the CPU 802, cause the example computing device 801 to conduct a visual acuity test.

Moreover, as noted above, after capturing one or more images of the evaluated person's EP pupils, the computing device 801 and/or other components of the vision screening device 104 may determine the evaluated persons refractive error. In such examples, the refractive error may be determined based at least partly on information related to the sphere, cylinder, axis, gaze angle, pupil diameter, interpupillary distance, and/or other characteristics of the evaluated person EP. Once such a refractive error is determined, the computing device 801 and/or other components of the vision screening device 104 may estimate the evaluated person's EP visual acuity based at least partly on the refractive error. In some examples, however, the computing device 801 and/or other components of the vision screening device 104 may utilize additional information in estimating the evaluated person's EP visual acuity.

Figure 15:
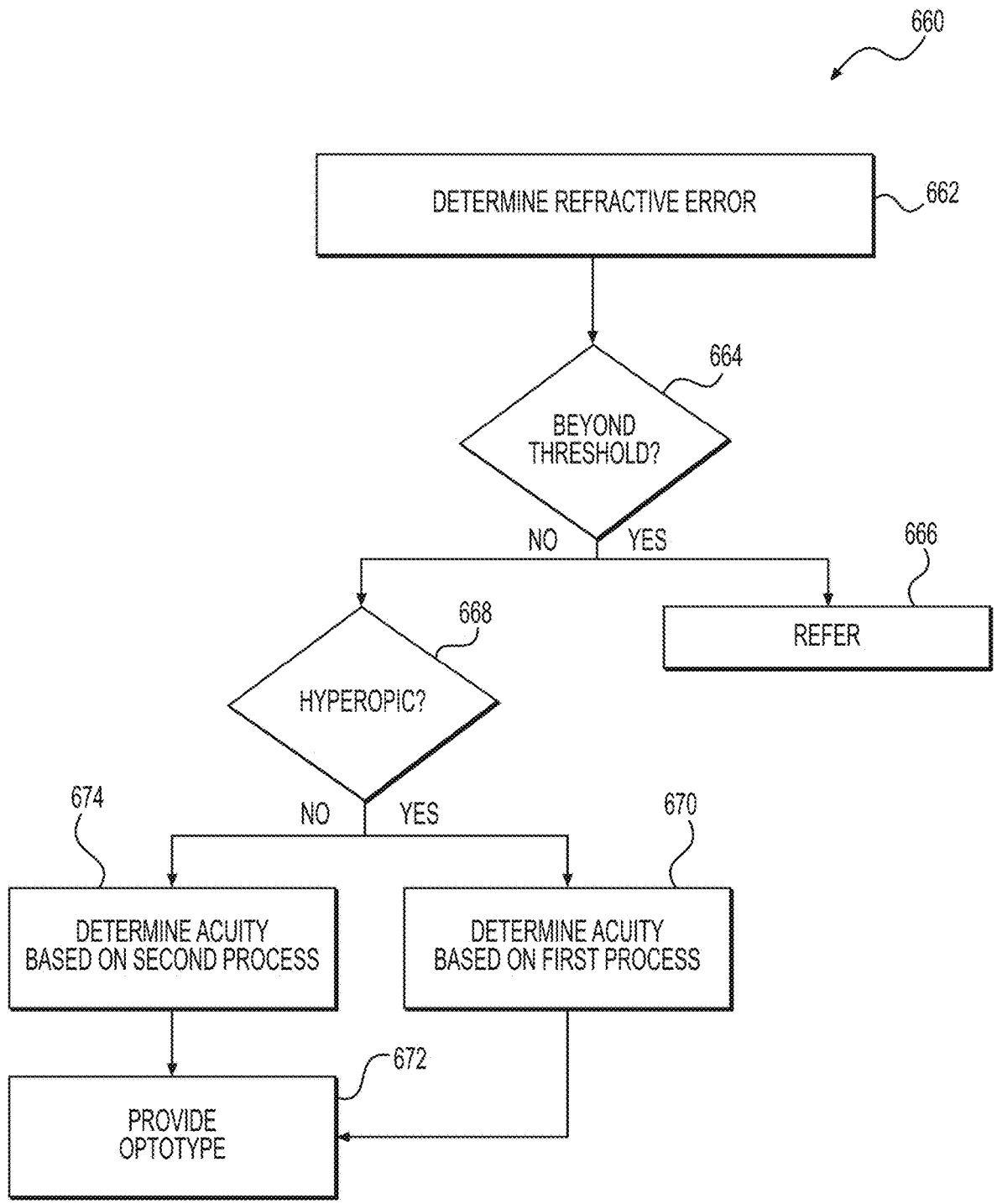
FIG. 15 shows a flow chart illustrating another example method of the present disclosure.

For example, as illustrated with respect to the method 660 shown in FIG. 15, in some embodiments the vision screening device 104 may determine the refractive error of the evaluated person EP (operation 662) as described above with respect to at least FIGS. 5 and 6. The vision screening device 104 may then determine whether or not a refractive error value representative of the evaluated person's EP refractive error is beyond one or more predetermined thresholds (operation 664). For example, the vision screening device 104 may utilize an upper threshold of +3 and a lower threshold of −3 when evaluating refractive error testing results. In such examples, if the refractive error determination at 662 yields a value of +7 (or some other example value above the upper threshold), at 664 the vision screening device 104 may determine that the refractive error of the evaluated patient EP is beyond such an upper threshold (664—Yes), and as a result, the vision screening device 104 may provide an output to the user U (operation 666) indicating that the evaluated person EP should be referred to a vision specialist for further evaluation. Likewise, if the refractive error determination at 662 yields a value of −5 (or some other value below the lower threshold), at 664 the vision screening device 104 may determine that the refractive error of the evaluated person EP is beyond such a lower threshold (664—Yes), and as a result, the vision screening device 104 may provide an output to the user U (operation 666) indicating that the evaluated person EP should be referred to a vision specialist for further evaluation. It is understood that in other examples, different upper and/or lower threshold values may be used at 664.

If the refractive error determination at 662 yields a value that is greater than a lower threshold and less than an upper threshold (664—No), the vision screening device 104 may determine whether the refractive error determination and 662 yielded a value that is indicative of a hyperopic subject (operation 668). For example, if the refractive error determination at 662 yields a value that is greater than zero, such a value may indicate that the evaluated person EP is hyperopic (668—Yes). Based at least in part on such a determination, the vision screening device 104 may, at 670, determine the visual acuity of the evaluated person EP based on a first process. In some examples, such a first process may comprise utilizing one or more algorithms, data plots, graphs, lookup tables including empirical data, neural networks, and/or other items in order to determine the visual acuity. In particular, such a first process may cause the vision screening device 104 to determine a visual acuity of the evaluated person EP based at least in part on one or more of the refractive error, age, gender, sphere, cylinder, axis, ethnicity, pupilometry, and/or other characteristics of the evaluated person EP.

Figure 12:
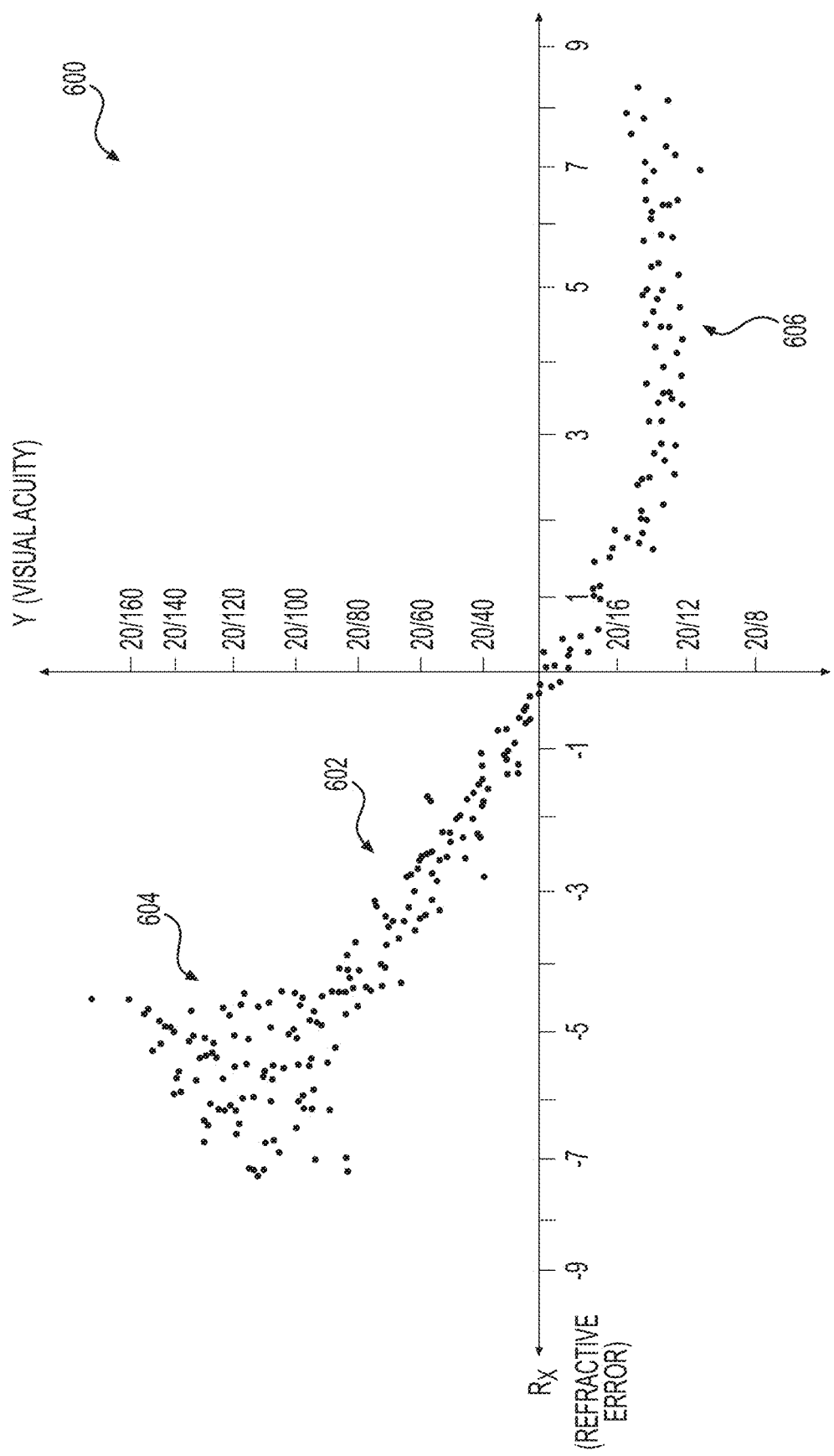
FIG. 12 illustrates a data plot including example refractive error values plotted against corresponding example visual acuity values.

For example, FIG. 12 illustrates a data plot 600 including example refractive error values plotted against corresponding visual acuity values. As shown in FIG. 12, a relatively direct linear relationship may exist (e.g., at portion 602 of the data plot 600) between refractive error and visual acuity for myopic subjects having a refractive error between approximately zero and approximately −5. Accordingly, a corresponding visual acuity for an evaluated person EP having a refractive error value in this range may be determined with relatively high confidence. Such a relationship may be more difficult to identify (e.g., at portion 604 of the data plot 600) for myopic subjects having a refractive error beyond (e.g., less than) approximately −5. Such a relationship may also be difficult to identify (e.g., at a portion 606 of the data plot 600) for hyperopic subjects (e.g., subjects having a refractive error value greater than approximately zero). Accordingly, for such hyperopic subjects, the vision screening device 104 may determine visual acuity at 670 by utilizing (e.g., as a function of) additional information associated with the evaluated person EP. Such example additional information is illustrated in FIGS. 13 and 14.

Figure 13:
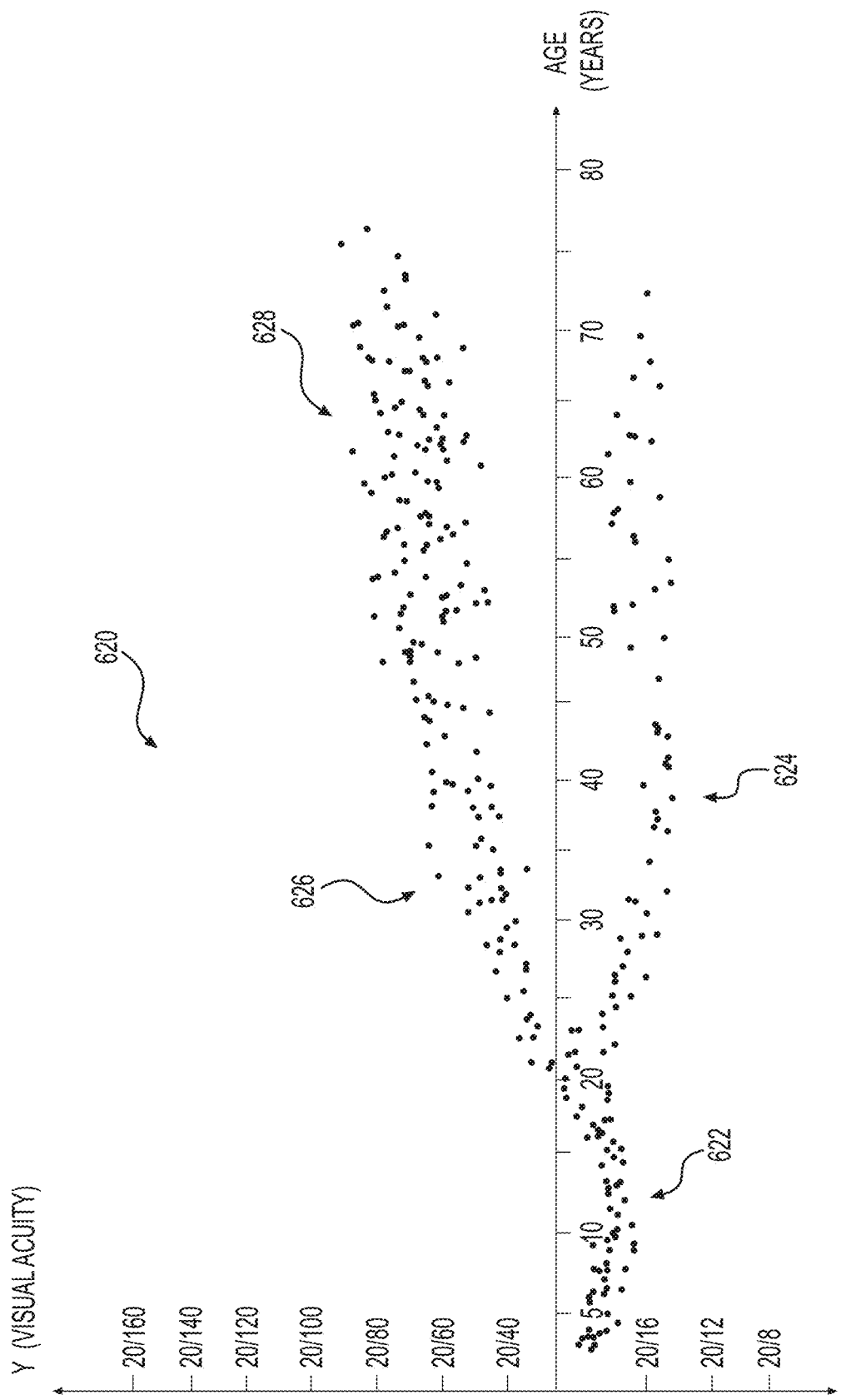
FIG. 13 illustrates a data plot including example visual acuity values plotted against corresponding example ages for evaluated persons.

For example, FIG. 13 illustrates a data plot 620 including example visual acuity values plotted against corresponding ages for evaluated subjects. As shown in FIG. 13, relatively young subjects (e.g., subjects below the age of 10, as identified at portion 622 of the data plot 620) may have a tendency to be hyperopic. Accordingly, in some example data sets (e.g., data sets associated with example clinical trials), a corresponding visual acuity for an evaluated person EP below the age of 10 may be estimated based at least in part on such data. As shown by the data illustrated at portion

624, in some example data sets, the tendency for hyperopia may decrease as age increases. Similarly, as shown by the data illustrated at portions 626 and 628, in some example data sets, the tendency for myopia may increase as age increases. It is understood that the example data represented in FIG. 13 is merely for discussion purposes, and in additional examples, other data may illustrate different relationships between, for example, visual acuity and age. Nevertheless, such information and/or relationships may be useful in determining the visual acuity of the evaluated person EP either alone or in combination with refractive error values and/or other characteristics of the evaluated person EP at 670.

Figure 14:
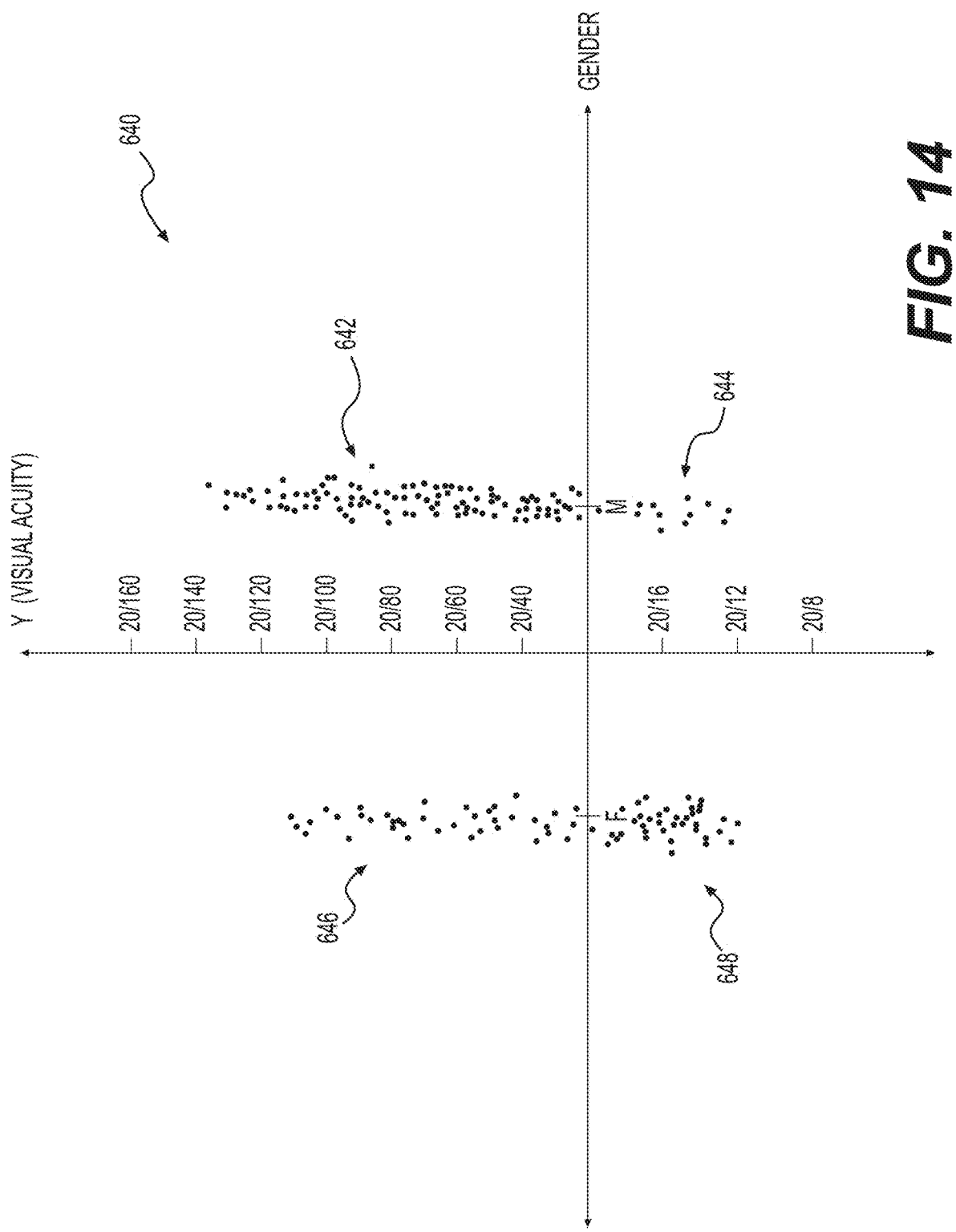
FIG. 14 illustrates a data plot including example visual acuity values plotted for example male and female subjects.

FIG. 14 illustrates a data plot 640 including example visual acuity values plotted for male and female subjects. As shown in FIG. 14, in some example data sets (e.g., data sets associated with example clinical trials), male subjects may have a tendency to be hyperopic (as illustrated by portions 642 and 644 of the data plot 640). Additionally, as shown by the data illustrated at portions 646 and 648, in some example data sets the tendency for hyperopia versus myopia may be relatively evenly distributed among female subjects. As noted above with respect to FIG. 13, the example data represented in FIG. 14 is merely for discussion purposes, and in additional examples, other data may illustrate different relationships between, for example, visual acuity and gender. Nevertheless, such information and/or relationships may be useful in determining the visual acuity of the evaluated person EP either alone or in combination with refractive error values and/or other characteristics of the evaluated person EP at 670.

For example, in some embodiments one or more algorithms, data plots, graphs, lookup tables including empirical data, neural networks, and/or other items may be utilized by the vision screening device 104 to determine the visual acuity of the evaluated person EP at 670. In such examples, the visual acuity of the evaluated person EP may be determined using one or more algorithms such as:

$$\text{Visual Acuity} = \text{Refractive Error}(A) + \text{Age}(B) + \text{Gender}(C) + X$$

where numerical values are used to represent refractive error, age, and gender, and where A, B, and C represent multipliers. In the above algorithm, X may comprise one or more additional functions, factors, or terms representing sphere, axis, cylinder, ethnicity, and/or other characteristics of the evaluated person EP. At 672, the vision screening device 104 may display and/or otherwise provide one or more optotypes to the evaluated person EP as described above with respect to at least FIGS. 7 and 8.

Alternatively, if the refractive error determination at 662 yields a value that is less than zero, such a value may indicate that the evaluated person EP is myopic (668—No). Based at least in part on such a determination, the vision screening device 104 may, at 674, determine the visual acuity of the evaluated person EP based on a second process. In some examples, such a second process may comprise utilizing one or more algorithms, data plots, graphs, lookup tables including empirical data, neural networks, and/or other items in order to determine the visual acuity. In particular, such a second process may cause the vision screening device 104 to determine a visual acuity of the evaluated person EP based at least in part on the refractive error of the evaluated person EP and/or in accordance with the relationship represented at least at portion 602 of the data plot 600 shown in FIG. 12. In such examples, the visual acuity of the evaluated person EP may be determined using one or more algorithms such as:

$$\text{Visual Acuity} = \text{Refractive Error}(A)$$

where a numerical value is used to represent refractive error, and where A represents an example multiplier. In such examples, at 672, the vision screening device 104 may display and/or otherwise provide one or more optotypes to the evaluated person EP as described above with respect to at least FIGS. 7 and 8.

The following clauses describe one or more example embodiments of the present disclosure, either alone or in combination:

A. A vision screening apparatus, comprising: a processing unit; and memory storing instructions that, when executed by the processing unit, cause the vision screening apparatus to: determine a Snellen equivalent based on an evaluation of a refractive error result; determine an evaluated person distance from the vision screening apparatus; based on the evaluated person distance and the Snellen equivalent, determine an adjusted optotype size; and display an optotype in the adjusted optotype size.

B. The vision screening apparatus according to clause A, the memory further storing instructions that, when executed by the processing unit, cause the vision screening apparatus to: perform a photorefraction ocular screening test, thereby generating the refractive error result; transmit a request to a server for the Snellen equivalent, the request including the refractive error result; and receive a response from the server, the response including the Snellen equivalent.

C. The vision screening apparatus according to at least one of the clauses noted above, the memory further storing instructions that, when executed by the processing unit, cause the vision screening apparatus to: receive an age of an evaluated person; and based on the age, adjust the optotype to an age-appropriate optotype, the age-appropriate optotype being displayed in the adjusted optotype size.

D. The vision screening apparatus according to at least one of the clauses noted above, the age-appropriate optotype including at least one of: an object, a shape, a number, and a letter.

E. The vision screening apparatus according to at least one of the clauses noted above 1, further comprising: a first display unit; a second display unit; an image sensor unit; the memory further storing instructions that, when executed by the processing unit, cause the vision screening apparatus to: display the refractive error result on the first display unit; and display the optotype on the second display unit.

F. The vision screening apparatus according to at least one of the clauses noted above, further comprising a range finder, the range finder being used for determining the evaluated person distance from the vision screening apparatus.

G. The vision screening apparatus according to at least one of the clauses noted above, the memory further storing instructions that, when executed by the processing unit, cause the vision screening apparatus to display a fogged optotype.

H. The vision screening apparatus according to at least one of the clauses noted above, the evaluated person distance being updated throughout a modified Snellen test.

I. The vision screening apparatus according to at least one of the clauses noted above, the adjusted optotype size being adjusted throughout the modified Snellen test.

J. The vision screening apparatus according to at least one of the clauses noted above, the Snellen equivalent being determined using at least one of: spherical equivalent, sphere, cylinder, axis, gaze angle, pupil diameter, and interpupillary distance.

K. A method for visual acuity screening with a vision screening apparatus, the method comprising: determining a refractive error; determining a Snellen equivalent to the refractive error; determining an optotype based on the Snellen equivalent; determining a distance of a person from the vision screening apparatus; based on the distance of the person from the vision screening apparatus, adjusting a size of the optotype, thereby generating an adjusted optotype; and displaying the adjusted optotype on a display of the vision screening apparatus.

L. The method according to at least one of the clauses noted above, further comprising: transmitting a request for the Snellen equivalent, the request including the refractive error being sent to a server; and receiving a response from the server, the response including the Snellen equivalent.

M. The method according to at least one of the clauses noted above, further comprising: receiving an age of the person; based on the age, adjusting the optotype to an age-appropriate optotype; and displaying the age-appropriate optotype in an adjusted optotype size.

N. The method according to claim 13, wherein displaying the age-appropriate optotype includes displaying at least one of: an object, a shape, a number, and a letter.

O. The method according to claim 11, further comprising displaying a defocused optotype.

P. A visual acuity screening apparatus, comprising: a processing unit; and memory storing instructions that, when executed by the processing unit, cause the visual acuity screening apparatus to: perform a photorefraction ocular screening test, thereby generating refractive error data; transmit a request to a server for a Snellen equivalent, the request including the refractive error data; and receive a response from the server, the response including the Snellen equivalent; determine an evaluated person distance from the visual acuity screening apparatus; based on the evaluated person distance and the Snellen equivalent, determine an adjusted optotype size; display an optotype in the adjusted optotype size; and display a fogged optotype.

Q. The visual acuity screening apparatus according to at least one of the clauses noted above, the memory further storing instructions that, when executed by the processing unit, cause the visual acuity screening apparatus to: receive an age of an evaluated person; and based on the age, adjust the optotype to an age-appropriate optotype, the age-appropriate optotype being displayed in the adjusted optotype size, the age-appropriate optotype including at least one of: an object, a shape, a number, and a letter.

R. The visual acuity screening apparatus according to at least one of the clauses noted above, further comprising: a first display unit; a second display unit; an image sensor unit; the memory further storing instructions that, when executed by the processing unit, cause the visual acuity screening apparatus to: display the refractive data result on the first display unit; and display the optotype on the second display unit.

S. The visual acuity screening apparatus according to at least one of the clauses noted above, further comprising a range finder, the range finder being used for determining the evaluated person distance from the visual acuity screening apparatus.

T. The visual acuity screening apparatus according to at least one of the clauses noted above, the evaluated person distance being updated throughout a modified Snellen test; the adjusted optotype size being adjusted throughout the modified Snellen test; and the Snellen equivalent being determined using at least one of: spherical equivalent, sphere, cylinder, axis, gaze angle, pupil diameter, and interpupillary distance.

In some instances, one or more components may be referred to herein as "configured to," "configurable to," "operable/operative to," "adapted/adaptable," "able to," "conformable/conformed to," etc. Those skilled in the art will recognize that such terms (e.g., "configured to") can generally encompass active-state components and/or inactive-state components and/or standby-state components, unless context requires otherwise.

The description and illustration of one or more embodiments provided in this application are not intended to limit or restrict the scope of the invention as claimed in any way. Regardless whether shown and described in combination or separately, the various features (both structural and methodological) are intended to be selectively included or omitted to produce an embodiment with a particular set of features. Having been provided with the description and illustration of the present application, one skilled in the art may envision variations, modifications, and alternate embodiments falling within the spirit of the broader aspects of the claimed invention and the general inventive concept embodied in this application that do not depart from the broader scope.

What is claimed is:

1. A vision screening apparatus, comprising:
   a processing unit;
   a range finder operably connected to the processing unit; and
   memory storing instructions that, when executed by the processing unit, cause the vision screening apparatus to:
      receive information indicating an acuity threshold associated with a group of people, the group of people including a person to be evaluated;
      determine a Snellen equivalent based on an evaluation of a refractive error result, the Snellen equivalent indicating a predicted visual acuity of the person;
      determine that the predicted visual acuity exceeds the acuity threshold;
      based on determining that the predicted visual acuity exceeds the acuity threshold, select an optotype size corresponding to the acuity threshold associated with the group of people;
      determine, using the range finder, a distance extending from the person to the vision screening apparatus;
      based on the distance and the optotype size, determine an adjusted optotype size; and
      display an optotype having the adjusted optotype size.

2. The vision screening apparatus according to claim 1, the memory further storing instructions that, when executed by the processing unit, cause the vision screening apparatus to:
   perform a photorefraction ocular screening test, thereby generating the refractive error result;
   transmit a request to a server for the Snellen equivalent, the request including the refractive error result; and
   receive a response from the server, the response including the Snellen equivalent.

3. The vision screening apparatus according to claim 1, the memory further storing instructions that, when executed by the processing unit, cause the vision screening apparatus to:
   receive an age of an evaluated person; and based on the age, adjust the optotype to an age-appropriate optotype, the age-appropriate optotype being displayed in the adjusted optotype size.

4. The vision screening apparatus according to claim 3, the age-appropriate optotype comprising a non-text optotype including at least one of:
an object and a shape.

5. The vision screening apparatus according to claim 1, further comprising:
a first display unit;
a second display unit;
an image sensor unit;
the memory further storing instructions that, when executed by the processing unit, cause the vision screening apparatus to:
display the refractive error result on the first display unit; and
display the optotype on the second display unit.

6. The vision screening apparatus according to claim 1, the instructions further causing the vision screening apparatus to:
perform a photorefraction ocular screening test, thereby generating the refractive error result;
select a visual acuity determination process, from a plurality of visual acuity determination processes, based on the refractive error result, the visual acuity determination process comprising one of:
a first process utilizing a component configured for use with a myopic evaluated person, or
a second process different from the first process and utilizing a component configured for use with a hyperopic evaluated person.

7. The vision screening apparatus according to claim 1, the memory further storing instructions that, when executed by the processing unit, cause the vision screening apparatus to display a fogged optotype.

8. The vision screening apparatus according to claim 1, the instructions further causing the visual acuity screening apparatus to:
generate movement instructions based on the evaluated person distance; and
output the movement instructions, the movement instructions indicating a desired change in the evaluated person distance.

9. The vision screening apparatus according to claim 1, wherein the adjusted optotype size comprises a dynamic size characterized by a dimension that is substantially continuously adjusted throughout a vision screening test, in real time, based on distances determined using the range finder.

10. The vision screening apparatus according to claim 1, the Snellen equivalent being determined using at least one of: spherical equivalent, sphere, cylinder, axis, gaze angle, pupil diameter, and interpupillary distance, and wherein causing the vision screening apparatus to display the optotype having the adjusted optotype size comprises causing the vision screening apparatus to display a single line of optotypes to the person, the optotypes in the single line of optotypes including having sizes substantially equivalent to the adjusted optotype size.

11. A visual acuity screening apparatus, comprising:
a processing unit;
a range finder operably connected to the processing unit; and
memory storing instructions that, when executed by the processing unit, cause the visual acuity screening apparatus to:
perform, on a person of a group of people, a photorefraction ocular screening test, thereby generating refractive error data associated with the person;
transmit a request to a server for a Snellen equivalent, the request including the refractive error data;
receive a response from the server, the response including the Snellen equivalent, the Snellen equivalent indicating a predicted visual acuity of the person;
receive information indicating an acuity threshold associated with the group of people;
determine that the predicted visual acuity exceeds the acuity threshold;
based on determining that the predicted visual acuity exceeds the acuity threshold, select an optotype size corresponding to the acuity threshold associated with the group of people;
determine, using the range finder, a distance extending from the person to the visual acuity screening apparatus;
based on the distance and the optotype size, determine an adjusted optotype size;
display an optotype having the adjusted optotype size; and
display a fogged optotype.

12. The visual acuity screening apparatus according to claim 11, the memory further storing instructions that, when executed by the processing unit, cause the visual acuity screening apparatus to:
receive an age of an evaluated person; and
based on the age, adjust the optotype to an age-appropriate optotype, the age-appropriate optotype being displayed in the adjusted optotype size, the age-appropriate optotype including at least one of: an object, a shape, a number, and a letter.

13. The visual acuity screening apparatus according to claim 12, further comprising:
a first display unit;
a second display unit;
an image sensor unit;
the memory further storing instructions that, when executed by the processing unit, cause the visual acuity screening apparatus to:
display the refractive data result on the first display unit; and
display the optotype on the second display unit.

14. The visual acuity screening apparatus according to claim 11, the instructions further causing the visual acuity screening apparatus to:
generate movement instructions based on the evaluated person distance; and
output the movement instructions, the movement instructions indicating a desired change in the evaluated person distance.

15. The visual acuity screening apparatus according to claim 14, the evaluated person distance being updated throughout a modified Snellen test;
the adjusted optotype size being adjusted throughout the modified Snellen test; and
the Snellen equivalent being determined using at least one of: spherical equivalent, sphere, cylinder, axis, gaze angle, pupil diameter, and interpupillary distance.

* * * * *